(12) United States Patent
Bartroli Orpi et al.

(10) Patent No.: US 6,653,475 B2
(45) Date of Patent: Nov. 25, 2003

(54) METHOD FOR PREPARING PYRIMIDONE DERIVATIVES WITH ANTIFUNGAL ACTIVITY

(75) Inventors: Javier Bartroli Orpi, Barcelona (ES); Manuel Anguita Lopez, Barcelona (ES)

(73) Assignee: J. Uriach & Cia, S.A., Barcelona (ES)

( * ) Notice: Subject to any disclaimer, the term of this patent is extended or adjusted under 35 U.S.C. 154(b) by 0 days.

(21) Appl. No.: 10/221,099

(22) PCT Filed: Mar. 5, 2001

(86) PCT No.: PCT/ES01/00081
§ 371 (c)(1),
(2), (4) Date: Sep. 9, 2002

(87) PCT Pub. No.: WO01/66519
PCT Pub. Date: Sep. 13, 2001

(65) Prior Publication Data
US 2003/0064986 A1 Apr. 3, 2003

(30) Foreign Application Priority Data
Mar. 7, 2000 (ES) .......................................... P 200000625

(51) Int. Cl.$^7$ .............................................. C07D 403/06
(52) U.S. Cl. ........................................ 544/284; 544/287
(58) Field of Search ................................ 544/284, 287

(56) References Cited

U.S. PATENT DOCUMENTS

| 5,116,844 A | 5/1992 | Dickinson et al. ....... 548/263.2 |
| 5,466,820 A | 11/1995 | Itoh et al. .................. 514/269 |

FOREIGN PATENT DOCUMENTS

WO    WO 97/05130    * 2/1997

OTHER PUBLICATIONS

Bartroli, Javier, et al., "New Azole Antifungals, 3. Synthesis and Antifungal Activity of 3–Substituted–4(3H)–quinazolinones," *J. Med. Chem.*, 1998, pp. 1869–1882, vol. 41. American Chemical Society.

* cited by examiner

*Primary Examiner*—Deepak Rao
(74) *Attorney, Agent, or Firm*—Rothwell, Figg, Ernst & Manbeck

(57) ABSTRACT

Process for the preparation of pyrimidone derivatives of formula I, which comprises reacting a compound of formula II with a compound of formula III in the presence of a base. The pyrimidone derivatives of formula I are useful as antifungal agents.

I

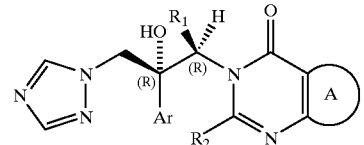

II

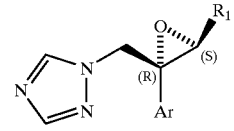

III

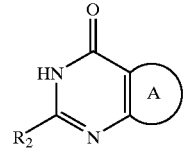

13 Claims, No Drawings

METHOD FOR PREPARING PYRIMIDONE DERIVATIVES WITH ANTIFUNGAL ACTIVITY

This application is a 371 of PCT/E501/00081 filed Mar. 5, 2001.

FIELD OF THE INVENTION

The present invention relates to a new process for the preparation of pyrimidone derivatives with antifungal activity.

DESCRIPTION OF THE INVENTION

Patent application WO 97/05130 describes a series of pyrimidone derivatives with potent antifungal activity. Amongst the compounds described in this patent, those optically active compounds with a stereochemistry (R,R) are preferred. A particularly preferred compound is (1R,2R)-7-chloro-3-[2-(2,4-difluorophenyl)-2-hydroxy-1-methyl-3-(1H-1,2,4-triazol-1-yl) propyl]quinazolin-4(3H)-one, which is known in the literature as UR-9825.

The process described to date for the preparation of these optically active pyrimidone derivatives suffers from certain disadvantages when considered for industrial scale application. It is therefore necessary to find an alternative process to prepare these optically active pyrimidone derivatives, and specially UR-9825.

DESCRIPITON OF THE INVENTION

The present invention thus relates to a new process for the preparation of pyrimidone derivatives of general formula I,

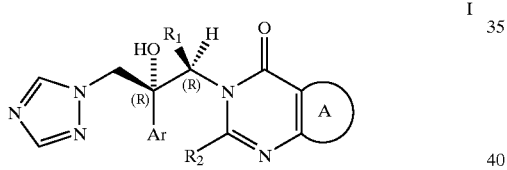

wherein:
Ar represents phenyl or phenyl substituted with one or more halogen and/or trifluoromethyl groups;
$R_1$ is $C_1$–$C_4$ alkyl;
$R_2$ represents hydrogen, $C_1$–$C_4$ alkyl, $C_1$–$C_4$ haloalkyl, or cyclopropyl;
A represents a benzene ring or a 5- or 6-membered heterocyclic ring wherein one or more of the ring atoms are selected from the group consisting of N, O and S, which rings can be optionally fused to a benzene ring or to a 5- or 6-membered heterocyclic ring containing one or more heteroatoms selected from N, O and S, and wherein A can be unsubstituted or have 1, 2, 3 or 4 substituents W in any of the rings;
a group W represents $C_1$–$C_4$ alkyl, $C_3$–$C_6$ cycloalkyl, $C_1$–$C_4$ haloalkyl, $C_1$–$C_4$ alkoxy, $C_1$–$C_4$ haloalkoxy, halogen, nitro, cyano, hydroxy, benzyloxy, hydroxymethyl, —$NR_3R_4$, —$CONR_3R_4$, —$CH_2$—$OCO$—$R_3$, —$CO$—$R_3$, —$COO$—$R_3$, —$SO_2R_5$, —$C(=NR_3)NHR_6$, —$C(=NR_6)OR_3$, and additionally one of the groups W can also represent 1-pyrrolyl, 1-imidazolyl, 1H-1,2,4-triazol-1-yl, 5-tetrazolyl (optionally substituted with $C_1$–$C_4$ alkyl), 1-pyrrolidinyl, 4-morpholinyl, 4-morpholinyl-N-oxide, a group —X—$R_7$, or a group of formula (i)–(iv):

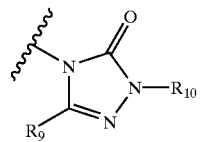

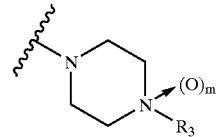

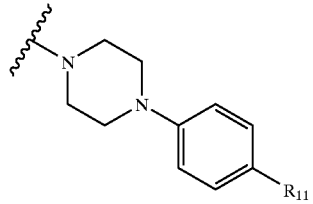

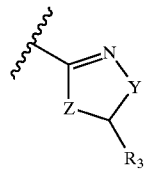

$R_3$ represents hydrogen, $C_1$–$C_4$ alkyl, $C_3$–$C_6$ cycloalkyl or aryl$C_1$–$C_4$ alkyl, wherein aryl represents phenyl or phenyl substituted with one or more $C_1$–$C_4$ alkyl, halogen, $C_1$–$C_4$ haloalkyl, $C_1$–$C_4$ alkoxy or $C_1$–$C_4$ haloalkoxy groups;
$R_4$ represents hydrogen, $C_1$–$C_4$ alkyl, $C_3$–$C_6$ cycloalkyl, —$COR_3$ or —$COCF_3$;
$R_5$ represents $C_1$–$C_4$ alkyl;
z represents 0, 1 or 2;
$R_6$ represents hydrogen, —$CONH_2$, —$COCH_3$, —$CN$, —$SO_2NHR_3$, —$SO_2R_3$, —$OR_3$, —$OCOR_3$ or —($C_{1-4}$ alkyl)—$NH_2$;
X represents a single bond, —O—, —$SO_z$—, —$NR_3$—, or —$C(=O)$—;
$R_7$ represents a phenyl group optionally substituted with one or more groups $R_8$;
$R_8$ represents $C_1$–$C_4$ alkyl, $C_3$–$C_6$ cycloalkyl, $C_1$–$C_4$ haloalkyl, $C_1$–$C_4$ alkoxy, $C_1$–$C_4$ haloalkoxy, halogen, nitro, cyano, —$NR_3R_4$, —$CONR_3R_4$, —$CH_2$—$OCO$—$R_3$, —$CO$—$R_3$, —$COO$—$R_3$, —$SO_zR_5$, —$C(=NR_3)NHR_6$, —$C(=NR_6)OR_3$, a group of formula (iv) or $R_8$ represents a phenyl group (optionally substituted with a $C_1$–$C_4$ alkyl, $C_1$–$C_4$ haloalkyl, $C_1$–$C_4$ alkoxy, $C_1$–$C_4$ haloalkoxy, halogen, nitro or cyano group);
$R_9$ represents hydrogen or methyl;
$R_{10}$ represents hydrogen, isopropyl, cyclopentyl, cyclopropyl, 2-butyl, 3-pentyl, 3-hydroxy-2-butyl, or 2-hydroxy-3-pentyl;
m represents 0 or 1;
$R_{11}$ represents halogen, $C_1$–$C_4$ haloalkyl, $C_1$–$C_4$ haloalkoxy, nitro, amino, cyano, or a group of formula (i);
Y represents —$CH_2$— or —$C(=O)$—; and
Z represents NH or O;

which comprises reacting a compound of formula II

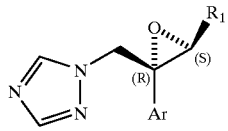

II wherein $R_1$ and Ar have the meaning defined above in relation to formula I, with a compound of formula III

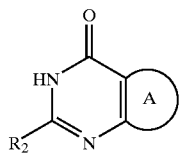

III wherein A and $R_2$ have the meaning defined above in relation to formula I, in the presence of a base.

In the above definitions, the term $C_1$–$C_4$ alkyl, as a group or part of a group, means a straight or branched alkyl group having from 1 to 4 carbon atoms. Therefore, it includes methyl, ethyl, propyl, isopropyl, butyl, isobutyl, sec-butyl, and tert-butyl.

A $C_1$–$C_4$ haloalkyl group means a group resulting from the substitution of one or more hydrogen atoms of a $C_1$–$C_4$ alkyl group with one or more halogen atoms (i.e. fluoro, chloro, bromo or iodo), which can be the same or different. Examples thereof include trifluoromethyl, trichloromethyl, fluoromethyl, chloromethyl, bromomethyl, iodomethyl, difluoromethyl, dichloromethyl, 2-chloroethyl, 2,2-dichloroethyl, 2,2,2-trichloroethyl, pentachloroethyl, 2-fluoroethyl, 2,2-difluoroethyl, 2,2,2-trifluoroethyl, pentafluoroethyl, 3-chloropropyl, 3,3-dichloropropyl, 3,3,3-trichloropropyl, 2,2,3,3,3-pentachloropropyl, 3-fluoropropyl, 3,3-difluoropropyl, 3,3,3-trifluoropropyl, 2,2,3,3-tetrafluoropropyl, 2,2, 3,3,3-pentafluoropropyl, heptafluoropropyl, 4-chlorobutyl, 4-fluorobutyl, 4-iodobutyl and 4-bromobutyl.

A $C_3$–$C_6$ cycloalkyl group represents cyclopropyl, cyclobutyl, cyclopentyl or cyclohexyl.

A $C_1$–$C_4$ alkoxy group means a group derived from the union of a $C_1$–$C_4$ alkyl group to an oxygen atom of an ether functional group. Examples include methoxy, ethoxy, propoxy, isopropoxy, butoxy, isobutoxy, sec-butoxy and tert-butoxy.

A $C_1$–$C_4$ haloalkoxy group means a group resulting from the substitution of one or more hydrogen atoms of a $C_1$–$C_4$ alkoxy group with one or more halogen atoms, which can be the same or different. Examples include trifluoromethoxy, fluoromethoxy, 2-chloroethoxy, 2-fluoroethoxy, 2-iodoethoxy, 2,2-difluoroethoxy, 2,2,2-trifluoroethoxy, pentafluoroethoxy, 3-fluoropropoxy, 3-chloropropoxy, 2,2,3, 3-tetrafluoropropoxy, 2,2,3,3,3-pentafluoropropoxy, heptafluoropropoxy, 4-fluorobutoxy, and 4-chlorobutoxy.

Halogen represents a fluoro, chloro, bromo or iodo atom.

An aryl$C_1$–$C_4$ alkyl group means a group resulting from the substitution of a hydrogen atom of a $C_1$–$C_4$ alkyl group with an aryl group, wherein aryl is as defined above.

In a preferred embodiment, in the preparation process which is the object of the invention $R_2$ represents hydrogen, methyl, trifluoromethyl or cyclopropyl; Ar represents 2-fluorophenyl, 4-fluorophenyl, 2-chloro-4-fluorophenyl, 2,4-dichlorophenyl, 2,4-difluorophenyl, 4-(trifluoromethyl) phenyl or 4-chlorophenyl; and A represents a benzene ring, which can be optionally fused to a benzene ring or to a 5- or 6-membered heterocyclic ring containing one or more heteroatoms selected from N, O and S, or A represents a 5- or 6-membered heterocyclic ring wherein one or more of said ring atoms are selected from the group consisting of N, O and S and which can be optionally fused to a benzene ring, wherein A can be unsubstituted or have 1, 2, 3 or 4 substituents W in any of the rings.

In a more preferred embodiment, $R_1$ represents methyl; $R_2$ represents hydrogen; Ar represents 2-fluorophenyl, 2,4-dichlorophenyl, 2,4-difluorophenyl, 4-(trifluoromethyl) phenyl or 4-chlorophenyl; and A represents a benzene ring or a 5- or 6-membered heterocyclic ring containing one or more heteroatoms selected from N, O and S, wherein A can be unsubstituted or have 1, 2, 3 or 4 groups W.

In a still more preferred embodiment, $R_1$ represents methyl; $R_2$ represents hydrogen; Ar represents 2-fluorophenyl, 2,4-dichlorophenyl, 2,4-difluorophenyl, 4-(trifluoromethyl)phenyl or 4-chlorophenyl; A represents a benzene ring optionally substituted with 1, 2, 3 or 4 groups W; and each W independently represents halogen, $C_1$–$C_4$ haloalkyl, $C_1$–$C_4$ haloalkoxy or cyano.

In a particularly preferred embodiment, the process of the invention is used to prepare a compound of formula I which is (1R,2R)-7-chloro-3-[2-(2, 4-difluorophenyl)-2-hydroxy-1-methyl-3-(1H-1,2,4-triazol-1-yl)propyl]quinazolin-4-(3H)-one (UR-9825) and it comprises reacting (2R,3S)-2-(2,4-difluorophenyl)-3-methyl-2-[(1H-1,2,4-triazol-1-yl) methyl]oxirane with 7-chloro-3H-quinazolin-4-one in the presence of a base.

The process for the preparation of the compounds of formula I which is the object of the invention can be summarized in the following scheme:

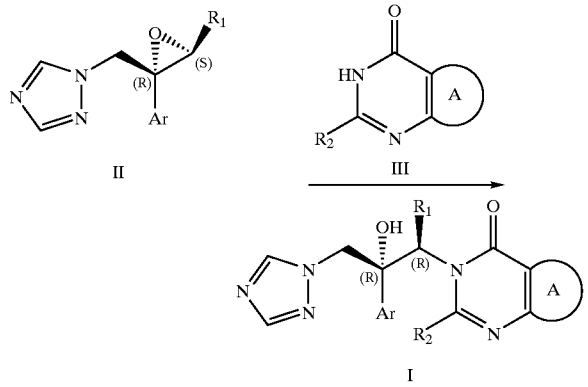

The reaction between an epoxide of formula II and a compound of formula III is carried out in the presence of a base, such as for example sodium hydride, potassium carbonate, butyllithium, sodium hexamethyldisilazane (NaHMDS), lithium hexamethyldisilazane (LiHMDS) or potassium hexamethyldisilazane (KHMDS), in a suitable solvent, such as for example a polar solvent such as a substituted amide (e.g. N-methylpyrrolidone or dimethylformamide) or an ether (e.g. tetrahydrofuran or dioxane), at a temperature preferably comprised between room temperature and that of the boiling point of the solvent.

The product of formula I thus obtained can be isolated in a conventional manner and can be purified by standard methods well known to those skilled in the art, such as for example by recrystallization from a suitable solvent.

The starting epoxides of formula II are known compounds and can be prepared using any of the methods already described, for example by following the process described by Tasaka et al. in *Chem. Pharm. Bull.* 1993, 41(6), 1035–1042.

The compounds of formula III can be prepared from the compounds of formula IV by reaction with a reactive derivative of an acid $R_2CO_2H$, such as its alkyl imidate (for example the methyl or ethyl imidate), its amidine, its acid chloride, its anhydride or its trialkylorthoester, preferably its amidine or trialkylorthoester, at a temperature generally over 50° C., as shown in the following scheme:

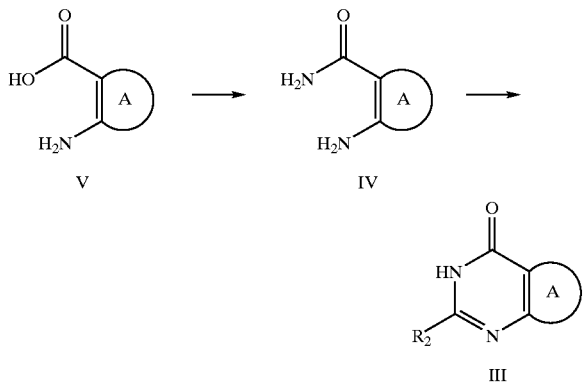

In its turn, the compounds of formula IV are either commercially available or can be prepared by conventional processes, for example from an acid of formula V by treatment with ammonium hydroxide in the presence of a suitable coupling agent, for example dicyclohexylcarbodiimide, alone or associated with 1-hydroxybenzotriazole, in a polar solvent, such as a substituted amide (for example N-methylpyrrolidone or dimethylformamide) or an ether (for example tetrahydrofuran or dioxane), at a temperature preferably comprised between 0° C. and 100° C., or from the corresponding nitrile, for example a benzonitrile, by hydrolysis under the standard conditions widely known to those skilled in the art.

The acids of formula V and of formula $R_2COOH$ or derivatives thereof are commercially available, are widely described in the literature or can be prepared by methods analogous to those described in the literature, for example as described in Bartroli et al. *J.Med.Chem.* 1998, 41, 1855–1868.

The invention is next illustrated with the following examples, which are not to be understood as limiting the scope of the present invention in any way.

EXAMPLE 1

2-Amino4-chlorobenzamide

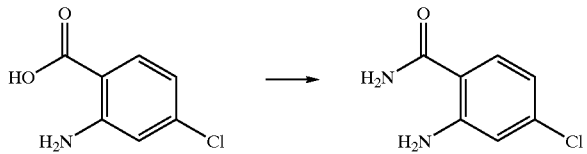

To a solution of 4-chloroanthranilic acid (70 g, 0.41 mol) in hot (60° C.) dimethylformamide (700 mL), dicyclohexylcarbodiimide (93 g, 0.451 mol, 1.1 equiv), hydroxybenzotriazole hydrate (60.9 g, 0.451 mol, 1.1 eq) and 30% aqueous ammonium hydroxide solution (350 mL) were added. The resulting solution was stirred at room temperature for 18 h.

The formed urea was filtered off and the filtrate concentrated. The resulting mixture was partitioned between ethyl acetate and 5% $K_2CO_3$ solution. The organic phase was separated, dried over anhydrous $Na_2SO_4$, filtered and the filtrate was concentrated to dryness to give the desired product as a slightly yellow solid (58.1 g, 83%).

mp 179–180° C.; $^1H$ NMR (300 MHz, MeOH—$d_4$) δ (MeOH) 7.46 (d, J=8.5 Hz, 1H, arom), 6.74 (d, J=2, 1H, arom), 6.53 (dd, J=2, J=8.5, 1H, arom). Analysis calculated for $C_7H_7ClN_2O$: C 49.28; H 4.14; N 16.42. Found: C 49.36; H 4.22; N 16.46.

EXAMPLE 2

7-Chloro-3H-quinazolin-4-one

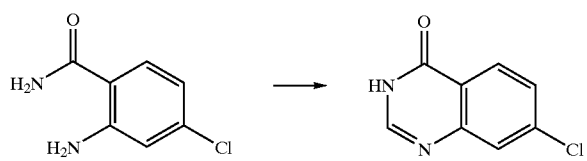

To a solution of 2-amino-4-chlorobenzamide (58 g, 0.34 mol) in hot (60° C.) N-methylpyrrolidone (170 mL), triethylorthoformate (151 g, 1.02 mol, 3 equiv) and a 1,4-dioxane 5N HCl solution (ca. 15 mL) were added. The resulting solution was heated at 110° C. for 18 h. Then, the mixture was cooled to room temperature, was poured over cold water and was brought to pH 7 with saturated $NaHCO_3$ solution. The formed precipitate was filtered, washed with water and dried to give the desired product as a slightly beige solid (58 g, 94%).

mp 253–256° C.; $^1H$ NMR (300 MHz, MeOH—$d_4$) δ (MeOH) 8.19 (d, J=8.6 Hz, 1H, arom), 8.10 (s, 1H, N=CH—N), 7.70 (d, J=2, 1H, arom), 7.54 (dd, J=2, J=8.6, 1H, arom). Analysis calculated for $C_8H_5ClN_2O$: C 53.21; H 2.79; N 15.51. Found: C, 53.46; H, 2.77; N, 15.48.

EXAMPLE 3

(1R,2R)-7-Chloro-3-[2-(2,4-difluorophenyl)-2-hydroxy-1-methyl-3-(1H-1,2, 4-triazol-1-yl)propyl]quinazolin-4(3H)-one (UR-9825)

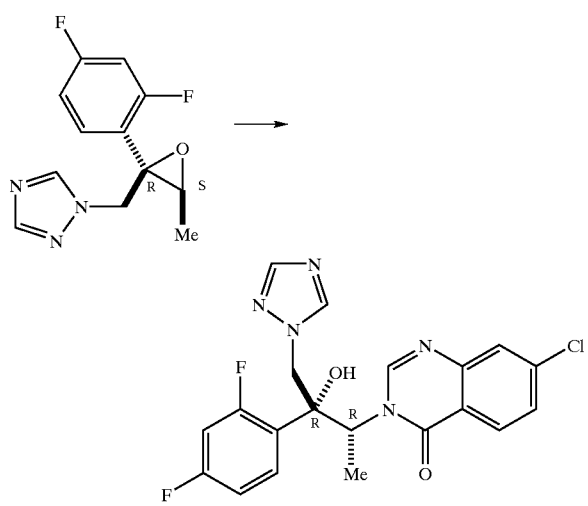

To a solution of (2R,3S)-2-(2,4-difluorophenyl)-3-methyl-2-[(1H-1,2,4-triazol-1-yl)methyl]oxirane (2.46 g, 9.8 mmol, obtained as described in Tasaka et al., *Chem.Pharm.Bull.* 1993, 41, 1035–1042) in N-methylpyrrolidone (10 mL), 7-chloro-3H-quinazolin-4-one (1.77 g, 9.8 mol) and $K_2CO_3$ (1.35 g, 9.8 mmol) were added. The resulting solution was heated at 80° C. for 3 days. The mixture was cooled to room temperature, water was then added and the pH was adjusted to 7. The mixture was extracted with ethyl acetate (4×). The combined organic extracts were washed with water (4×), dried over anhydrous $Na_2SO_4$ and filtered. The filtrate was concentrated to a reduced volume and was allowed to crystallize at 0° C. The resulting product was filtered, dried and dissolved in hot ethanol (10 mL/g). The insoluble material was filtered off, and the filtrate was then poured over cold water (120 mL/g of UR-9825) under stirring. The resulting precipitate was filtered and dried in vacuo (50° C.) to give the desired product as a white amorphous powder (3.1 g, 75%).

mp 93–110° C. (amorphous); IR (KBr) v 1675, 1601, 1554, 1498 $cm^{-1}$; $^1$H NMR (300 MHz, $CDCl_3$) δ (TMS) 8.58 (s, 1H, N=CH—N), 8.26 (d, J=8.6 Hz, 1H, arom), 8.11 (d, J=5.7, trace rotamer), 7.76 (s, 2H, triazole), 7.74 (d, J=5.3, 1H, arom), 7.5 (m, 2H, arom), 7.10 (s, trace rotamer), 6.9–6.7 (m, 2H, arom), 5.91 (dq, $J_d$=2, $J_q$=7, 1H, MeCH), 5.54 (d, J=2, 1H, OH), 5.15 (d, J=14.2 1H, CH(H)), 4.9–4.7 (m, trace rotamer), 4.30 (d, trace rotamer), 3.99 (d, J=14.2, 1H, CH(H)), 1.46 (d, J=6.9, trace rotamer), 1.29 (d, J=7, 3H, CHMe); GC/MS 224 (Tr—$CH_2$COHAr, $C_{10}H_8F_2N_3O$), 207 (N-ethylheterocycle group, $C_{10}H_9CIN_2O$); $[α]_D$=−8.0° (c 1, $CHCl_3$). Analysis calculated for $C_{20}H_{16}ClF_2N_5O_2$: C 55.63; H 3.73; N 16.22. Found: C 55.50; H 3.75; N 16.16.

What is claimed is:

1. A process for the preparation of pyrimidone derivatives of general formula I,

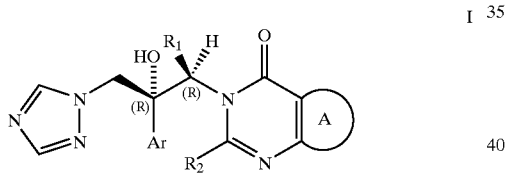

wherein:
Ar represents phenyl or phenyl substituted with one or more halogen and/or trifluoromethyl groups;
$R_1$ is $C_1$–$C_4$ alkyl;
$R_2$ represents hydrogen, $C_1$–$C_4$ alkyl, $C_1$–$C_4$ haloalkyl, or cyclopropyl;
A represents a benzene ring or a 5- or 6-memberd heterocyclic ring wherein one or more of the ring atoms are selected from the group consisting of N, O and S, which benzene or heterocyclic ring optionally can be fused to a benzene ring or a 5- or 6-membered heterocyclic ring containing one or more heteroatoms selected from N, O and S, and wherein A can be unsubstituted or have 1, 2, 3 or 4 substituents W on any of the rings;
a group W represents $C_1$–$C_4$ alkyl, $C_3$–$C_6$ cycloalkyl, $C_1$–$C_4$ haloalkyl, $C_1$–$C_4$ alkoxy, $C_1$–$C_4$ haloalkoxy, halogen, nitro, cyano, hydroxy, benzyloxy, hydroxymethyl, —$NR_3R_4$, —$CONR_3R_4$, —$CH_2$—OCO—$R_3$, —CO—$R_3$, —COO—$R_3$, —$SO_zR_5$, —C(=$NR_3$) $NHR_6$, —C(=$NR_6$) $OR_3$, and additionally one of the groups W can also represent 1-pyrrolyl, 1-imidazolyl, 1H-1,2,4-triazol-1-yl, 5-tetrazolyl (optionally substituted with $C_1$–$C_4$ alkyl), 1-pyrrolidinyl, 4-morpholinyl, 4-morpholinyl-N-oxide, a group —X—$R_7$, or a group of formula (i)–(iv):

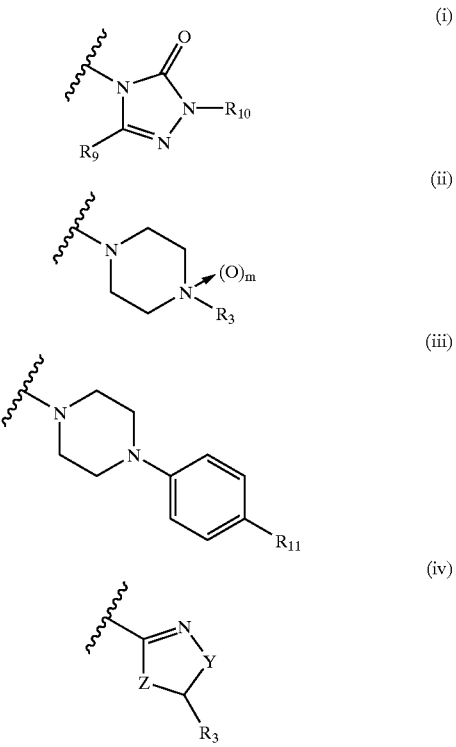

$R_3$ represents hydrogen, $C_1$–$C_4$ alkyl, $C_3$–$C_6$ cycloalkyl or aryl$C_1$–$C_4$ alkyl, wherein aryl represents phenyl or phenyl substituted with one or more $C_1$–$C_4$ alkyl, halogen, $C_1$–$C_4$ haloalkyl, $C_1$–$C_4$ alkoxy or $C_1$–$C_4$ haloalkoxy groups;
$R_4$ represents hydrogen, $C_1$–$C_4$ alkyl, $C_3$–$C_6$ cycloalkyl, —$COR_3$ or —$COCF_3$;
$R_5$ represents $C_1$–$C_4$ alkyl;
z represents 0, 1 or 2;
$R_6$ represents hydrogen, —$CONH_2$, —$COCH_3$, —CN, —$SO_2NHR_3$, —$SO_2R_3$, —$OR_3$, —$OCOR_3$ or —($C_{1-4}$ alkyl)—$NH_2$;
X represents a single bond, —O—, —$SO_z$—, —$NR_3$—, or —C(=O)—;
$R_7$ represents a phenyl group optionally substituted with one or more groups $R_8$;
$R_8$ represents $C_1$–C4 alkyl, $C_3$–$C_6$ cycloalkyl, $C_1$–$C_4$ haloalkyl, $C_1$–$C_4$ alkoxy, $C_1$–$C_4$ haloalkoxy, halogen, nitro, cyano, —$NR_3R_4$, —$CONR_3R_4$, —$CH_2$—OCO—$R_3$, —CO—$R_3$, —COO—$R_3$, —$SO_zR_5$, —C(=$NR_3$)$NHR_6$, —C(=$NR_6$)$OR_3$, a group of formula (iv) or $R_8$ represents a phenyl group (optionally substituted with a $C_1$–$C_4$ alkyl, $C_1$–$C_4$ haloalkyl, $C_1$–$C_4$ alkoxy, $C_1$–$C_4$ haloalkoxy, halogen, nitro or cyano group);
$R_9$ represents hydrogen or methyl;
$R_{10}$ represents hydrogen, isopropyl, cyclopentyl, cyclopropyl, 2-butyl, 3-pentyl, 3-hydroxy-2-butyl, or 2-hydroxy-3-pentyl;
m represents 0 or 1;
$R_{11}$ represents halogen, $C_1$–$C_4$ haloalkyl, $C_1$–$C_4$ haloalkoxy, nitro, amino, cyano, or a group of formula (i);
Y represents —$CH_2$— or —C(=O)—; and Z represents NH or O;
which comprises reacting a compound of formula II

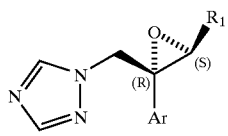

wherein $R_1$ and Ar have the meaning defined above in relation to formula I, with a compound of formula III

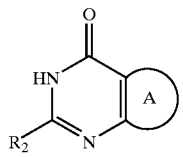

wherein A and $R_2$ have the meaning defined above in relation to formula I, in the presence of a base.

2. A process according to claim 1 wherein $R_2$ represents hydrogen, methyl, trifluoromethyl or cyclopropyl; Ar represents 2-fluorophenyl, 4-fluorophenyl, 2-chloro-4-fluorophenyl, 2,4-dichlorophenyl, 2,4-difluorophenyl, 4-(trifluoromethyl)phenyl or 4-chlorophenyl; and A represents a benzene ring, which optionally can be fused to a benzene ring or to a 5- or 6-membered heterocyclic ring containing one or more heteroatoms selected from N, O and S, or A represents a 5- or 6-membered heterocyclic ring wherein one or more of said ring atoms are selected from the group consisting of N, O and S and which optionally can be fused to a benzene ring, wherein A can be unsubstituted or have 1, 2, 3 or 4 substituents W in any of the rings.

3. A process according to claim 1 wherein $R_1$ represents methyl; $R_2$ represents hydrogen; Ar represents 2-fluorophenyl, 2,4-dichlorophenyl, 2,4-difluorophenyl, 4-(trifluoromethyl)phenyl or 4-chlorophenyl; and A represents a benzene ring or a 5- or 6-membered heterocyclic ring containing one or more heteroatoms selected from N, O and S, wherein A can be unsubstituted or have 1, 2, 3 or 4 groups W.

4. A process according to claim 1 wherein $R_1$ represents methyl; $R_2$ represents hydrogen; Ar represents 2-fluorophenyl, 2,4-dichlorophenyl, 2,4-difluorophenyl, 4-(trifluoromethyl)phenyl or 4-chlorophenyl; A represents a benzene ring optionally substituted with 1, 2, 3 or 4 groups W; and each W independently represents halogen, $C_1$–$C_4$ haloalkyl, $C_1$–$C_4$ haloalkoxy or cyano.

5. A process according to claim 1 wherein the compound of formula I is (1R,2R)-7-chloro-3-[2-(2,4-difluorophenyl)-2-hydroxy-1-methyl-3-(1H-1,2,4-triazol-1-yl)propyl]quinazolin-4(3H)-one.

6. A process according to claim 1, 2, 3, 4 or 5 wherein the base is sodium hydride, potassium carbonate, butyllithium, sodium hexamethyldisilazane (NaHMDS), lithium hexamethyldisilazane (LiHMDS) or potassium hexamethyldisilazane (KHMDS).

7. A process according to claim 1, 2, 3, 4 or 5 wherein the reaction is carried out in a polar solvent.

8. A process according to claim 7 wherein the polar solvent is a substituted amide or an ether.

9. A process according to claim 8 wherein the solvent is N-methylpyrrolidone, dimethylformamide, tetrahydrofuran or dioxane.

10. A process according to claim 1, 2, 3, 4 or 5 wherein the reaction is carried out at a temperature comprised between room temperature and that of the boiling point of the solvent.

11. A process for the preparation of (1R,2R)-7-chloro-3-[2-(2,4-difluorophenyl)-2-hydroxy-1-methyl-3-(1H-1,2,4-triazol-1-yl)propyl]quinazolin-4(3H)-one which comprises reacting (2R,3S)-2-(2,4-difluorophenyl)-3-methyl-2-[(1H-1,2,4-triazol-1-yl)methyl]oxirane with 7-chloro-3H-quinazolin-4-one in the presence of a base.

12. A process according to claim 1 wherein the base is sodium hydride, potassium carbonate, butyllithium, sodium hexamethyldisilazane (NaHMDS), lithium hexamethyldisilazane (LiHMDS) or potassium hexamethyldisilazane (KHMDS) and the reaction is carried out in a polar solvent and at a temperature comprised between room temperature and that of the boiling point of the solvent.

13. A process according to claim 1, 2, 3, 4, 5, 11 or 12 wherein the compound obtained is purified by recrystallization.

* * * * *